United States Patent [19]

Malabarba et al.

[11] Patent Number: 5,869,449
[45] Date of Patent: Feb. 9, 1999

[54] 38-DECARBOXY-38-HYDROXYMETHYL DERIVATIVES OF TEIOCOPLANIN ANTIBIOTICS AND A PROCESS FOR PREPARING THEM

[75] Inventors: Adriano Malabarba, Binasco; Romeo Ciabatti, Novate Milanese, both of Italy

[73] Assignee: Gruppo Lepetit S.P.A., Varese, Italy

[21] Appl. No.: 872,461

[22] Filed: Jun. 10, 1997

Related U.S. Application Data

[63] Continuation of Ser. No. 625,787, Mar. 29, 1996, abandoned, which is a continuation of Ser. No. 479,899, Jun. 7, 1995, abandoned, which is a continuation of Ser. No. 356,036, Dec. 14, 1994, abandoned, which is a continuation of Ser. No. 50,466, May 13, 1993, abandoned.

[30] Foreign Application Priority Data

Dec. 5, 1990 [EP] European Pat. Off. .............. 90123299

[51] Int. Cl.$^6$ .......................... A61K 38/12; C07K 11/02
[52] U.S. Cl. .................................... 514/11; 514/9; 514/8; 514/2; 530/317; 530/322; 530/321; 530/345; 930/190
[58] Field of Search ..................... 530/317, 345, 530/322, 321; 514/11, 9, 8, 2; 930/190

[56] References Cited

U.S. PATENT DOCUMENTS

| | | | |
|---|---|---|---|
| 4,239,751 | 12/1980 | Coronelli et al. | 424/118 |
| 4,542,018 | 9/1985 | Borghi et al. | 424/119 |
| 4,594,187 | 6/1986 | Strazzolini et al. | 530/332 |
| 4,629,781 | 12/1986 | Strazzolini et al. | 530/317 |
| 4,650,855 | 3/1987 | Malabarba et al. | 530/332 |
| 4,782,042 | 11/1988 | Selva et al. | 514/9 |
| 4,789,661 | 12/1988 | Malabarba et al. | 514/8 |
| 4,868,171 | 9/1989 | Selva et al. | 514/183 |
| 4,882,419 | 11/1989 | Malabarba et al. | 530/317 |
| 4,914,187 | 4/1990 | Malabarba et al. | 530/317 |
| 4,935,238 | 6/1990 | Selva et al. | 424/118 |
| 4,954,483 | 9/1990 | Malabarba et al. | 514/9 |
| 5,064,811 | 11/1991 | Borghi et al. | 514/8 |
| 5,085,990 | 2/1992 | Lancini et al. | 435/71.3 |
| 5,185,320 | 2/1993 | Trani et al. | 514/8 |
| 5,194,424 | 3/1993 | Malabarba et al. | 514/8 |
| 5,198,418 | 3/1993 | Malabarba et al. | 514/8 |
| 5,438,117 | 8/1995 | Malabarba et al. | 530/317 |
| 5,500,410 | 3/1996 | Malabarba et al. | 514/8 |
| 5,521,155 | 5/1996 | Malabarba et al. | 514/8 |
| 5,567,676 | 10/1996 | Selva et al. | 514/8 |
| 5,602,229 | 2/1997 | Malabarba et al. | 530/317 |
| 5,606,036 | 2/1997 | Hermann et al. | 536/4.1 |
| 5,644,025 | 7/1997 | Malabarba et al. | 530/317 |
| 5,648,456 | 7/1997 | Malabarba et al. | 530/317 |
| 5,674,840 | 10/1997 | Malabarba et al. | 514/9 |

FOREIGN PATENT DOCUMENTS

| | | |
|---|---|---|
| 0273727 | 7/1988 | European Pat. Off. .............. 530/317 |
| 0 276 740 A1 | 8/1988 | European Pat. Off. . |
| 0 290 922 A2 | 11/1988 | European Pat. Off. . |
| 0 316 712 A2 | 5/1989 | European Pat. Off. . |
| 0 326 873 A2 | 8/1989 | European Pat. Off. . |
| 0 351 597 A2 | 1/1990 | European Pat. Off. . |
| 0 351 684 A2 | 1/1990 | European Pat. Off. . |
| 0 351 685 A2 | 1/1990 | European Pat. Off. . |
| 0 352 538 A2 | 1/1990 | European Pat. Off. . |
| 0 370 283 A2 | 5/1990 | European Pat. Off. . |
| 0 448 940 A2 | 2/1991 | European Pat. Off. . |

OTHER PUBLICATIONS

Jentoft et al, The Journal of Biological Chemistry, vol. 254(11), pp. 4359–4365 (Jun. 10, 1979).

The Merck Manual of Diagnosis & Therapy, 11$^{th}$ ed., pp. 799–802, (1966).

*Primary Examiner*—Ponnathapura Achutamurthy
*Assistant Examiner*—T. D. Wessendorf
*Attorney, Agent, or Firm*—Killworth, Gottman, Hagan, & Schaeff, L.L.P.

[57] ABSTRACT

The present invention is directed to novel 38-decarboxy-38-hydroxymethyl derivatives of teicoplanin antiobiotics and a process for preparing them which includes submitted the corresponding lower alkyl ester precursor to a reduction reaction in the presence of an alkali metal borohydride. The compounds of the invention show an improved antibacterial activity against some clinical isolates of Staphylococci somewhat resistant to teicoplanin.

The teicoplanin derivatives of the present invention are represented by the following formula:

wherein:
  X represents hydroxymethyl;
  R represents hydrogen or —N[($C_9$–$C_{12}$)aliphatic acyl]-β-D-2-deoxy-2-aminoglucopyranosyl;
  $R_1$ represents hydrogen or N-acetyl-β-D-2-deoxy-2-aminoglucopyranosyl;
  $R_2$ represents hydrogen of alpha-D-mannopyranosyl;
  $R_3$ represents hydrogen or a protecting group of the amino function; and the acid addition salts thereof; with the proviso that $R_1$ represents hydrogen only when R and $R_2$ are simultaneously hydrogen.

17 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Xaa  Xaa  Xaa  Xaa  Xaa  Xaa
1                  5

38-DECARBOXY-38-HYDROXYMETHYL DERIVATIVES OF TEIOCOPLANIN ANTIBIOTICS AND A PROCESS FOR PREPARING THEM

This is a continuation of application Ser. No. 08/625,787, filed Mar. 29, 1996, now abandoned, which a continuation of application Ser. No. 08/479,899, filed Jun. 7, 1995, now abandoned, which is a continuation of application Ser. No. 08/356,036, filed Dec. 14, 1994, now abandoned, which is a continuation of application Ser. No. 08/050,466, filed May 13, 1993, now abandoned, which is herein incorporated by reference.

The present invention is directed to a new class of teicoplanin derivatives, a process for preparing them and their use as pharmaceutically active substances. The teicoplanin derivatives of the invention are represented by the following formula:

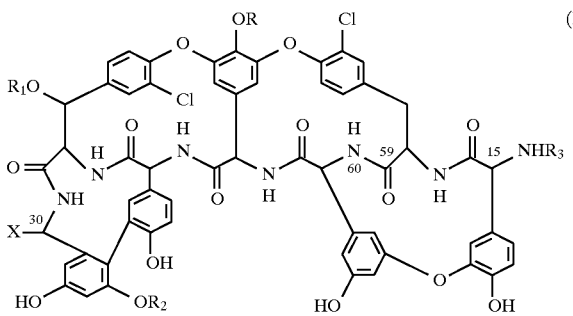

wherein:
X represents hydroxymethyl;
R represents hydrogen or —N[($C_9$–$C_{12}$)aliphatic acyl]-β-D-2-deoxy-2-aminoglucopyranosyl;
$R_1$ represents hydrogen or N-acetyl-β-D-2-deoxy-2-aminoglucopyranosyl;
$R_2$ represents hydrogen or alpha-D-mannopyranosyl;
$R_3$ represents hydrogen or a protecting group of the amino function; and the acid addition salts thereof; with the proviso that $R_1$ represents hydrogen only when R and $R_2$ are simultaneously hydrogen.

The novel antibiotic substances possess antimicrobial activity mainly against gram-positive bacteria (e.g. Staphylococcus and Streptococcus strains) and, in particular, against some clinical isolates of Staphylococcus somewhat resistant to teicoplanin. The novel antibiotic substances of the invention are obtained by chemical transformation of a protected lower alkyl ester derivative of a teicoplanin compound or of a teicoplanin-like compound or of mixtures thereof, and more precisely by a reduction reaction by an alkali-metal borohydride in the presence of water as solvent.

Teicoplanin is the international non-proprietary name (INN) of the antibiotic substance formerly named teichomycin which is obtained by cultivating the strains *Actinoplanes teichomyceticus* nov. sp. ATCC 31121 in a culture medium containing assimilable sources of carbon, nitrogen and inorganic salts (see U.S. Pat. No. 4,239,751).

According to the procedure described in the above cited patent, an antibiotic complex (identified as teichomycin) containing factors $A_1$, $A_2$ and $A_3$ is recovered from the fermentation broth by extraction with a suitable water insoluble organic solvent and precipitation from the organic solvent according to common procedures.

Factor $A_2$, which is the preponderant factor of the isolated antibiotic complex, is then separated from the other factors by means of column chromatography on Sephadex$^R$. Factor $A_1$ and factor $A_3$ are present only in minor amounts. British Patent No. 2121401 discloses that antibiotic factor $A_2$, in turn, actually is a mixture of five closely related co-produced main components.

From fermentation and purification (for instance, through column chromatography) operations a teicoplanin product is currently obtained which essentially consists of factor $A_2$ accompanied by minor amounts of factor $A_3$. It is known that teicoplanin factor $A_2$ and its individual components may be represented by the above described formula I wherein X is COOH (i.e. a carboxy function is present in position 38 of the molecule), R, $R_1$ and $R_2$ represent the cited sugar moieties, and $R_3$ is hydrogen.

More particularly, in teicoplanin $A_2$ component 1, the [($C_9$–$C_{12}$)-aliphatic acyl] moiety of the symbol R represents Z-4-decenoyl, in teicoplanin $A_2$ component 2 represents 8-methylnonanoyl, in teicoplanin $A_2$ component 3 represents decanoyl, in teicoplanin $A_2$ component 4 represents 8-methyldecanoyl, in teicoplanin $A_2$ component 5 represents 9-methyldecanoyl.

All the sugar moieties identified above are linked to the core/molecule through O-glycosidic bonds. A substance having the same structural core is disclosed in European Patent Application Publication No. 0090578 and is named antibiotic A 41030 factor B. This substance is obtained by means of a microbiological process which involves the fermentation of the strain *Streptomyces virginiae* NRRL 12525 or *Streptomyces virginiae* NRRL 15156 in a suitable medium, the isolation, purification and separation into its components of antibiotic A 41030, an antibiotic complex of at least seven factors, antibiotic A 41030 factor B, included.

In the European Patents No. 119574 and 119575 have been described partial hydrolysis products of teicoplanin factor $A_2$ wherein one or two sugar moieties are split off. These products are respectively named antibiotic L 17054 and L 17046. The products are obtained by submitting teicoplanin factor $A_2$ to same specific acid hydrolysis conditions. For L 17054 the hydrolysis is preferably carried out by using 0.5N hydrochloric acid at a temperature between 70° C. and 90° C. for 15 to 90 minutes. For L 17046, the hydrolysis is preferably carried out by using hydrochloric acid at a concentration from 1N to 3N at a temperature between 70° C. and 90° C. for 30 to 60 minutes.

Antibiotic L 17054 (teicoplanin pseudoaglycon 1) may be represented by the formula I above, whereby R is replaced by hydrogen, $R_1$ is a N-acetyl-D-glucosamine moiety, $R_2$ is a D-mannose moiety and X is a carboxy moiety. Antibiotic L 17046 (teicoplanin pseudoaglycon 2) may be represented by the formula I above wherein R and $R_2$ are both replaced by hydrogen, $R_1$ is a N-acetyl-D-glucosamine rest and X is a carboxy moiety. European Patent Application Publication No. 301247 describes the de-mannosyl teicoplanin derivatives, i.e. compounds of the formula I above wherein R and $R_1$ are as above, $R_2$ is hydrogen and X is a carboxy moiety.

European Patent Application Publication No. 146053 describes a chemical process for preparing antibiotic L 17392 (deglucoteicoplanin i.e. the compound of formula I wherein R, $R_1$, and $R_2$ are simultaneously hydrogen atoms and X is a carboxy moiety) by submitting a teicoplanin compound or a teicoplanin like compound to controlled strong acid hydrolysis characterized in that an organic protic solvent is used.

According to the disclosure of European Patent Application Publication No. 146053 it is also necessary to employ a strong acid compatible with the solvent such as a strong mineral acid or a strong organic acid, and carry out the reaction at a temperature between about 20° C. and about 100° C.

In this specification and claims, with the term "teicoplanin compound" it is indicated a substance selected from the teicoplanin complex obtained by fermentation of *Actinoplanes teichomyceticus* ATCC 31121 followed by purification operations according to U.S. Pat. No. 4,239,751, any further purified preparation thereof, teicoplanin factor $A_2$, teicoplanin factor $A_3$, each of the main components of teicoplanin factor $A_2$. The term "teicoplanin compounds" includes also teicoplanin RS-1 and RS-2 described in the paper given by M. Zanol et al, at the 17th International Symposium on Chromatography, Vienna Sep. 25–30, 1988 and teicoplanin RS-3 (compound A) and RS-4 (compound B) described in European Patent Application Publication No. 306645. These compounds may be represented through the formula I above wherein $R_1$ and $R_2$ are as above, the aliphatic acyl moiety of the radical R are respectively 10-methyl-undecanoyl, dodecanoyl, 6-methyl-octanoyl and nonanoyl and X is a carboxy moiety. With the term "teicoplanin-like compound" it is hereby indicated any compound having the same basic structure formula I as above wherein X is a carboxy moiety, R is hydrogen or a N-[($C_9$–$C_{12}$)aliphatic acyl]-D-glucosamine rest, $R_1$ is hydrogen or a N-acetyl-D-glucosamine moiety, $R_2$ is hydrogen or a D-mannose moiety with the proviso that $R_1$ represents hydrogen only when R and $R_2$ are simultaneously hydrogen, and a mixture of two or more of any of the above substances and/or compounds in any proportion.

European Patent Application Publication No. 216775 describes ester derivatives of deglucoteicoplanin and a chemical process for preparing them which essentially comprises submitting a teicoplanin compound or a teicoplanin like compound to a controlled esterification procedure by reacting it with an excess of alcohol in the presence of an acid catalyst at a temperature preferably comprised between 50° C. and 80° C. and, if necessary, selectively hydrolyzing the sugar substituents linked to the molecule.

European Patent Application Publication No. 182157 describes ester derivatives of antibiotic L 17046 and a process for preparing them. In a preferred embodiment of the process disclosed in European Patent Application Publication No. 182157 the antibiotic L 17046, appropriately protected, is reacted with a substituted alkyl halide in an inert organic polar protic solvent preferably in the presence of a hydrogen halide acceptor at a temperature from about −5° C. to 50° C. Teicoplanin pseudo aglycon methyl ester is also described in J. Am. Chem Soc. Vol. 106, No. 17, 1984. Synthesis and biological activity of some esters of the N-Acetyl glucosaminyl aglycon and of the aglycon of teicoplanin are described also in J. Antibiotics 40; 1572–1587, 1987. Lower alkyl ester derivatives of teicoplanin compounds may be easily prepared according to the above cited European Patent Applications Publication Nos 216775 and 182157. All the lower alkyl ester derivatives described above can be used as suitable starting materials in the process of the invention.

Preferred lower alkyl ester derivatives are those compounds of formula I wherein X represents —$COOR_4$ and $R_4$ is a linear or branched ($C_1$–$C_4$)alkyl group. More preferably $R_4$ is methyl or ethyl.

As it is mentioned above, the five main components of teicoplanin $A_2$ complex are characterized by the fact that the aliphatic acyl moiety of the β-D-2-deoxy-2-aminoglucopyranosyl moiety is: (Z)-4-decenoyl, 8-methylnonanoyl, decanoyl, 8-methyldecanoyl or 9-methyldecanoyl.

Accordingly, these substances can be used as starting material for the manufacture of the compounds of this invention either as individual products or as mixtures of two or more products. Since said starting materials for the preparation of the compounds of this invention can be used in both said form, the resulting end products may, in turn, be individual compounds or mixtures of two or more compounds of the above formula I. These mixtures of compounds are also part of the invention and may be used as such for their biological applications and uses or may be eventually separated in their individual components by known procedures described in the art. Examples of separation procedures suitable for the purposes of obtaining individual components from end products mixtures of 38-decarboxy-38-hydroxymethyl teicoplanin derivatives are those described in the following documents: European Patent Application Publication No. 218099 and International Patent Application Publication No. WO 88/06600.

The 38-decarboxy-38-hydroxymethyl teicoplanin derivatives can be prepared according to a higher selective reductive hydrolysis process which constitutes a further object of the present invention.

Said process includes submitting a compound of formula II

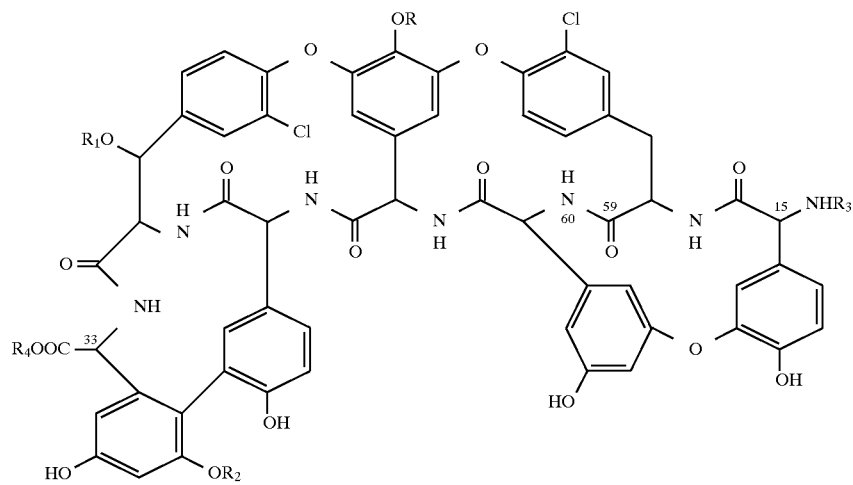

wherein, $R_4$ is ($C_1$–$C_4$)alkyl, $R_3$ is a protecting group of the amino function and R, $R_1$, $R_2$ are as defined above, or mixtures thereof, to a reduction reaction in the presence of an alkali metal borohydride preferably selected from sodium borohydride, potassium borohydride and sodium cyanoborohydride, at a temperature comprised between 0° C. and 40° C. using water as solvent.

The use of water as solvent is a critical aspect of the reductive process described above. However, when using a starting material which cannot be completely dissolved in water (e.g. the methyl ester aglycon of teicoplanin), a water/mixable organic co-solvent, preferably a lower alkyl alcohol, must be added. In such cases, the hydroalcoholic medium is a mixture of $H_2O$ and a lower alkanol, preferably methanol or ethanol, wherein the ratio $H_2O$/alcohol ranges between 90/10 v/v and 40/60 v/v, more preferably between 70/30 v/v and 50/50 v/v. In a representative embodiment of the invention by using the methyl ester of the aglycon of teicoplanin as starting material a ratio of $H_2O$/alcohol 50/50 v/v was used.

Sometimes, in particular cases, a small amount of a further organic polar co-solvent can be added to completely dissolve the starting material during the course of the reaction, e.g. N,N-dimethylformamide, 1,3-dimethyl-3,4,5,6-tetrahydro-2(1H)-pyrimidone (DMPU), dimethylsulfoxide.

As alkali metal borohydride the sodium borohydride is the most preferred one. The suitable amount of alkali metal borohydride employed may vary depending on the particular compound used as starting material, on the solvent used and on the temperature of the reaction, but it is advisable to use an amount of alkali metal borohydride in a large excess over the stoichiometric requirement in such a way that the pH of the reaction mixture is alkaline, preferably between pH 8 and 10. Anyway, in general, the molar ratio between the alkali metal borohydride and the antibiotic starting material is comprised between 50 and 300.

The reaction temperature may vary considerably depending on the specific starting materials and reaction conditions. In general, it is preferred to conduct the reaction at a temperature between 0° C. and 40° C., more preferably at room temperature. Also the reaction time may vary considerably depending on the other reaction parameters. In general, the reaction is completed in about 10–48 hours. In any case, the reaction course is monitored by TLC or, preferably, by HPLC according to methods known in the art. On the basis of the results of these assays a man skilled in the art will be able to evaluate the reaction course and decide when to stop the reaction and start working up the reaction mass according to known per se techniques which include, for instance, extraction with solvents, precipitation by addition of non-solvents, etc., in conjunction with further separations and purifications by column chromatography, when needed.

After the reaction is completed, in most cases, but not necessarily in all cases, depending on the starting material, a clear solution is formed; then the excess of the alkali metal borohydride is eliminated by adding a suitable amount of an acid, for example, a diluted mineral acid, e.g. hydrochloric, hydrobromic, and the like, a $(C_1-C_4)$alkyl organic acid, a $(C_1-C_6)$alkyl sulfonic acid, an aryl sulfonic acid and the like, dissolved in a polar protic solvent such as, for example a $(C_1-C_4)$alkyl alcohol.

A further aspect of the process of this invention is that the amino function in position 15 of the starting material must be protected before carrying out the reduction process. The N-protecting group which may be used in the process of the present invention is one of the N-protecting groups known in the art such as those described in reference books (see for instance T. W. Greene, "Protective Groups in Organic Synthesis", John Wiley and Sons, New York, 1981, p. 323–326, and M. Mc. Omie "Protecting Groups in Organic Chemistry", Plenum Press, New York, 1973) and which is capable of forming a bond with the amino groups of the teicoplanin-like derivatives which is stable at the conditions of the reaction process, does not unfavourably interfere with the reductive reaction, and is easily cleavable from the reaction product, without altering the newly formed 38-decarboxy-38-hydroxymethyl moiety, at the end of the reaction process.

Representative examples of N-protecting groups which may be advantageously used in the process of the invention are carbamate forming reagents characterized propyl by the following oxycarbonyl groups: 1,1-dimethyloxycarbonyl, t-butyloxycarbonyl, vinyloxycarbonyl, allyloxycarbonyl, cinnamyloxycarbonyl, 4,5-diphenyl-3-oxazolin-2-one, benzyloxycarbonyl, p-nitrobenzyloxycarbonyl, 3,4-dimethoxy-6-nitrobenzyloxycarbonyl, 2,4-dichlorobenzyloxycarbonyl, 5-benzisoxazolylmethyloxycarbonyl, 9-anthrylmethyloxycarbonyl, diphenylmethyl oxycarbonyl, isonicotinyloxycarbonyl, S-benzyloxy-carbonyl, and the like.

A particular preferred protecting group is t-butyloxycarbonyl. The N-protected final compounds can be then N-deprotected according to the techniques known in the art, for instance by treatment with trifluoroacetic acid (TFA).

In order to better emphasize the striking aspect of the process of the invention it is necessary to underline that in general, previous attempts to reduce the free-terminal carboxy group of teicoplanin using various complex metal hydrides failed. Also the methyl ester derivatives of these antibiotics were somewhat resistant to treatment with such reducing agents in anhydrous organic solvents. In some cases, e.g. using lithium borohydride in tetrahydrofuran, the reduction occurred with simultaneous epimerization of the final products thus making them completely inactive.

Furthermore, in the European Patent Application No. 90113139 it is disclosed that when an unprotected methyl ester teicoplanin compound is treated with an alkali metal borohydride using various $H_2O$-ethanol solvent mixtures the reductive cleavage of the peptidic bond between the second and the third aminoacid (position 59–60 of the amide bonds) and the formation of hydroxymethyl ester in position 38 simultaneously was observed.

Therefore it was not easy to find the right precursor and the optimal conditions to obtain the 38-hydroxy teicoplanin derivatives of the invention without modifying the critical structural core of the molecule. As outlined before the 38-decarboxy-38-hydroxymethyl teicoplanin derivatives of the invention having one or more sugar moieties split off, can be prepared from the corresponding ester precursor.

However, in addition, the sugar moiety of a 38-decarboxy-38-hydroxymethyl compound of formula I may be selectively removed to transform it into another 38-decarboxy-38-hydroxymethyl compound of formula I.

For example, a compound of formula I wherein R, $R_1$, and $R_2$ represent a sugar moiety as above defined can be transformed into the corresponding compound wherein $R_1$ and $R_2$ are as above and R is hydrogen by means of controlled acid hydrolysis in a strong concentrated aqueous organic acid. The concentrated organic acid in this case is preferably aqueous trifluoroacetic acid at a concentration between 75% and 95%, and the reaction temperature is preferably between 10° C. and 50° C. The preferred hydrolysis conditions are represented by about 90% trifluoroacetic acid at room temperature. The reaction time varies depending on the other specific reaction parameters but, in any case, the reaction may be monitored by TLC or preferably HPLC techniques. An analogous selective hydrolysis is reported in the European Patent No. 146822.

Similarly, compounds of formula I wherein R, $R_1$, and $R_2$ represent a sugar moiety as above defined or R represents hydrogen and $R_1$ and $R_2$ represent sugar moieties as above defined can be transformed into the corresponding compounds of formula I wherein R and $R_2$ represent hydrogen and $R_1$ represent a sugar moiety as defined by means of a selective hydrolysis with a strong acid in the presence of a polar aprotic solvent selected from ethers, ketones, and mixture thereof which are liquid at room temperature. Preferred hydrolysis conditions are in this case represented by the use of a concentrated mineral acid in the presence of an ether such as dimethoxyethane at room temperature. Also in this case, the reaction course may be monitored by TLC or preferably HPLC. An analogous selective hydrolysis is reported in the European Patent No. 175100.According to another embodiment of the present invention, a 38-decarboxy-38-hydroxymethyl compound of formula I wherein R, $R_1$ and $R_2$ represent sugar moieties as defined above, a compound of formula I wherein R represents hydrogen and $R_1$ and $R_2$ represent the above defined sugar moieties, or a compound of formula I wherein R and $R_2$ represent hydrogen, and $R_1$ represents a sugar moiety as above defined may be transformed into the corresponding compound of formula I wherein R, $R_1$ and $R_2$ represent hydrogen atoms by means of a selective hydrolysis in an organic protic solvent selected from aliphatic acids and alpha-halogenated aliphatic acids which at the reaction temperature are liquids, aliphatic and cycloaliphatic alkanols which at the reaction temperature are liquids slightly mixable with water, phenyl substituted lower alkanols wherein the phenyl moiety may optionally carry $(C_1-C_4)$alkyl, $(C_1-C_4)$alkoxy or halo moieties which at the reaction temperature are liquids slightly mixable with water, and β-polyhalogenated lower alkanols, which at the reaction temperature are liquids, in the presence of a strong acid, compatible with the solvent, selected from strong mineral acids, strong organic acids and strong acid cation exchange resins in the hydrogen form and at a temperature between 20° C. and 100° C. In this case, the preferred hydrolysis conditions are represented by the use of a mineral acid, such as hydrochloric acid, in a haloalkanol such as trifluoroethanol, at a temperature between 65° C. and 85° C.

Analogous selective hydrolysis conditions on a similar substrate are described in the already cited European Patent Application Publication No. 146053.

The 38-decarboxy-38-hydroxymethyl teicoplanin antibiotics of this invention can be isolated as free bases or as addition salts with acids. Representative acid addition salts are those formed by reaction with both inorganic and organic acids, for example, hydrochloric, sulfuric, phosphoric, succinic, citric, lactic, maleic, fumaric, cholic, d-glutamic, d-camphoric, glutaric, phthalic, tartaric, methanesulfonic, benzenesulfonic, benzoic, salicylic, trifluoroacetic acid and the like.

The addition salts with pharmacologically acceptable acids are particularly preferred.

The 38-decarboxy-38-hydroxymethyl teicoplanin derivatives of the present invention show antibacterial activity against Staphylococcus and Streptococcus strains.

The positive effect of the reduction of the carboxy group is particularly evident by comparing the activity of the 38-decarboxy-38-hydroxymethyl teicoplanin $A_2$ component 2 (MIC=0.25 mcg/ml) with that of teicoplanin $A_2$ component 2 (MIC=32 mcg/ml) against a strain of *S. epidermidis* which is one of the most frequently isolated coagulase-negative Staphylococcus strain in infections developed in hospitalized patients.

However what it is particularly surprising is that the 38-decarboxy-38-hydroxymethyl derivatives of teicoplanin are also more active than the corresponding methyl ester starting materials against some clinical isolates of Staphylococci which usually are resistant to teicoplanin.

The antibiotic activity of the compounds of the invention is demonstrated in vitro by means of standard two-fold dilution tests in microtiter, using Difco Todd-Hewitt broth or Oxoid Iso-Sensitest broth. Broth cultures are diluted enough so that the final inoculum is about $10^5$ colony forming units/ml (CFU/ml). Minimal inhibitory concentration (MIC) is considered as the lowest concentration which shows no visible growth after 18–24 h incubation at 37° C. Some representative results are reported in the following TABLE I, which illustrates the biological activity of representative 38-hydroxy-methyl teicoplanin antibiotics of the invention against clinical isolates of *S. epidermidis S. aureus* and *S. haemolyticus*.

TABLE I

Biological Activity of 38-Decarboxy-38-Hydroxymethyl Teicoplanin Derivatives
IN VITRO (MIC, mcg/ml) against some strains of Staphylococci (S.).

| Organism | | Compound | | | | |
|---|---|---|---|---|---|---|
| Internal No. | Strain | CTA/2 Me/ester | HM-CTA/2 | HM-TB | HM-TC | HM-TD |
| 561 | *S. aureus* clin. isolate | 4 | 4 | 2 | 0.5 | 0.13 |
| 147 | *S. epidermidis* ATCC 12228 | 0.5 | 0.13 | 1 | 0.063 | 0.063 |
| 533 | *S. epidermidis* clin. isolate | 4 | 0.25 | 2 | 0.13 | 0.13 |
| 602 | *S. haemolyticus* clin. isolate | 8 | 4 | 8 | 2 | 0.25 |

CTA/2 Me-ester: Form.I: X = COOMe; R = 8-methylnonanoyl-β-D-glucosaminyl; $R_1$ = N-Acetyl-β-D-glucosaminyl; $R_2$ = α-D-Mannosyl; $R_3$ = H (starting material)
HM CTA/2: Form.I: X = $CH_2OH$; R = 8-methylnonanoyl-β-D-glucosaminyl; $R_1$ = N-Acetyl-β-D-glucosaminyl; $R_2$ = α-D-Mannosyl; $R_3$ = H
HM-TB: Form.I: X = $CH_2OH$; R = $R_3$ = H; $R_1$ = N-Acetyl-β-D-glucosaminyl; $R_2$ = α-D-Mannosyl;
HM-TC: Form.I: X = $CH_2OH$; R = $R_2$ = H; $R_1$ = N-Acetyl-β-D-glucosaminyl; $R_3$ = H
HM-TD: Form.I: X = $CH_2OH$; R = $R_1$ = $R_2$ = $R_3$ = H

EXPERIMENTAL SECTION

In Table II for each compound the raw formula, the equivalent and the molecular weight are reported. All derivatives were analyzed for C, H, N, and Cl, on samples previously dried at 140° C. under $N_2$ atmosphere. The analytical results were within ±0.4% of the theoretical values.

Acid-base titrations were carried out under the following conditions: the sample was dissolved in a mixture methyl cellosolve (MCS) $H_2O$ 4/1, then an excess of 0.01M HCl in the same solvent mixture was added and the resulting solution was titrated with 0.01N NaOH. Acid-base titration indicated that the products of the invention possess one basic ionizable function with pK MCS 6.6–6.9 (See TABLE II).

Table III shows $^1H$ NMR data. $^1H$ NMR spectra were recorded (in DMSO-$d_6$) on a BRUKER AM 500 NMR-spectrometer equipped with an ASPECT 3000 computer, using $Me_4Si$ (80.00 ppm) as internal reference. Modified standard pulse sequences were used for 2 D NMR experiments.

The structures of the 38-decarboxy-38-hydroxymethyl teicoplanin derivatives maintain the characteristics $^1H$ and $^{13}C$ spectra of the parent antibiotic precursors except for proton at C-38, which is significantly shifted to higher field by about 0.4 ppm and shows in the COSY spectrum the expected coupling with the newly introduced alcoholic function (38—$CH_2$, $\delta \cong 3.72$ ppm). Inverse $^1H^{13}C$ correlation experiments confirmed these results. The products were purified by reverse-phase column chromatography on silanized Silica-gel (0.063–0.2 mm; Merck). Reactions, column eluates, and final products were checked by HPLC analyses which were performed on a column HIBAR RT 250-4 (Merck) pre-packed with LiChrosorb RP-8 (10 μm), using a VARIAN Model 5500 LC pump equipped with a 20, μl loop injector RHEODYNE Model 7125 and a VARIAN Model 2050 UV variable detector. Chromatograms were recorded at 254 nm. Elution was carried out at a flow rate of 2 ml/min by mixing eluent a, 0.2% aqueous $HCO_2NH_4$, with eluent b, $CH_3CN$, according to a linear step gradient from 20% to 60% of b in a in 30 minutes.

HPLC analysis (TABLE IV) shows that these derivatives are less lipophilic than corresponding teicoplanins methyl esters, but they are more lipophilic than the parent unmodified antibiotics.

TABLE II

| Compound Example No. | FORMULA | E.W. | M.W. | $pK_{MCS}$ |
|---|---|---|---|---|
| 1 | $C_{88}H_{99}N_9O_{32}Cl_2$ | 1990 | 1865.7 | 6.9 |
| 2 | $C_{72}H_{70}N_8O_{27}Cl_2$ | 1710 | 1550.3 | 6.9 |
| 3 | $C_{66}H_{60}N_8O_{22}Cl_2$ | 1515 | 1388.3 | 6.8 |
| 4 | $C_{58}H_{47}N_7O_{17}Cl_2$ | 1240 | 1185.0 | 6.6 |

E.W. equivalent weight determined by titration
M.W. molecular weight calculated from the assigned formula

TABLE III $^1$H-NMR Data (in DMSO-$d_6$; TMS internal standard, $\delta$ 0.00 ppm)

| COMPOUND Example No. | ($^1H$, $\delta$ ppm) |
|---|---|
| 1 | 0.82, 1.11, 1.45, 2.00 (N-acyl chain); 1.87 (acetylglucosamine); 3.42 (mannose); 3.72 (38-$CH_2$—OH); 4.12–5.54 (peptidic CH's); 6.28–8.53 (aromatic protons and peptidic NH's). |
| 2 | 1.85 (acetylglucosamine); 3.43 (mannose); 3.72 (38-$CH_2OH$); 4.06–5.82 (peptidic CH's); 6.08–8.52 (aromatic protons and peptidic NH's). |
| 3 | 3.41 (mannose); 3.72 (38-$CH_2OH$); 4.12–5.65 (peptidic CH's); 6.78–8.58 (aromatic protons and peptidic NH's). |
| 4 | 3.72 (38-$CH_2OH$); 4.14–5.76 (peptidic CH's); 6.23–8.48 (aromatic protons and peptidic NH's). |

TABLE IV

HPLC

| Compound Example No. | $t_R$ (min) |
|---|---|
| 1 | 10.1 |
| 2 | 4.5 |
| 3 | 6.3 |
| 4 | 8.2 |

In view of the above reported antimicrobial activity, the compounds of the present invention can effectively be employed as the active ingredient of antimicrobial preparations used in human and veterinary medicine for the prevention and treatment of infectious diseases caused by pathogenic bacteria which are susceptible to said active ingredients.

In such treatments, these compounds may be employed as such or in the form of mixtures in any proportion. The compounds of the present invention can be administered orally, topically or parenterally wherein however, the parenteral administration is preferred. Depending on the route of administration, these compounds can be formulated into various dosage forms. Preparations for oral administration may be in the form of capsules, tablets, liquid solutions or suspensions.

As known in the art the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions, may contain conventional additives such as suspending agents. For topical use the compounds of the present invention may also be prepared in suitable forms for absorption through the mucous membranes of the nose and throat or bronchial tissues and may conveniently take the form of liquid spray or inhalates, lozenges, or throat paints.

For medication of the eyes or ears, the preparation may be presented in liquid or semi-liquid form. Topical applications may be formulated in hydrophobic or hydrophilic bases as ointments, creams, lotions, paints, or powders.

For rectal administration the compounds of the invention are administered in the form of suppositories admixed with conventional vehicles, such as, for example, cocoa butter, wax, spermaceti or polyethylenglycols and their derivatives.

Compositions for injection may take such forms as suspensions, solutions, or emulsions in oily or aqueous vehicles, and may contain formulatory agents such as suspending, stabilizing and/or dispersing agents. Alternatively, the active ingredient may be in powder form for reconstitution at the time of delivery with a suitable vehicle, such as sterile water.

The amount of active principle to be administered depends on various factors such as the size and conditions of the subject to be treated, the route and frequency of administration, and the causative agent involved.

The compounds of the invention are generally effective at a dosage comprised between about 0.5 and about 30 mg of active ingredient per Kg of body weight, preferably divided in 2 to 4 administrations per day. Particularly desirable compositions are those prepared in the form of dosage units containing from about 20 to about 300 mg per unit.

A representative example of preparation of a pharmaceutical composition is a parenteral solution which is prepared with 100 mg of compound No. 1 dissolved in 1 ml of sterile water for injection.

Besides their activity as medicaments, the compounds of the present invention can be used as animal growth promoters.

For this purpose, one or more of the compounds of the invention is administered orally in a suitable feed. The exact concentration employed is that which is required to provide for the active agent in a growth promotant effective amount when normal amounts of feed are consumed.

The addition of the active compounds of the invention to animal feed is preferably accomplished by preparing an appropriate feed premix containing the active compounds in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and Co., S. Francisco, USA, 1969 or "Livestock Feeds and Feedings", O and B Books, Corvallis, Oreg., USA, 1977) and are incorporated herein by reference. The following Examples further illustrate the invention and must not be construed as limiting it.

PREPARATION OF THE STARTING MATERIALS.

A) $N^{15}$-tert-butyloxycarbonyl teicoplanin $A_2$ component 2 [($N^{15}$-t-BOC CTA/2] (Formula I: X=COOH, R=8-methylnonanoyl-β-D-glucosaminyl; $R_1$=N-Acetyl-β-glucosaminyl; $R_2$=α-D-Mannosyl).

To a stirred solution of 95 g (about 50 mmol) of teicoplanin $A_2$ component 2 (CTA/2) in 350 ml of $Me_2SO$, 12 ml (about 87 mmol) of triethylamine (TEA) and 24 g (about 80 mmol) of tert-butyl-2,4,5-trichlorophenyl carbonate were added at room temperature. After 5 hours, the reaction mixture was poured into 2 l of $H_2O$. The resulting solution was adjusted at pH 3 with 1N HCl and then extracted with 2 l of a butanol (BuOH): ethyl acetate 1:2 (v/v) mixture. The organic layer was separated, washed with 1 liter of $H_2O$, afterwards it was concentrated to a small volume (about 200 ml) at 35° C. under reduced pressure. On adding ethyl acetate (800 ml), the precipitated solid was collected (100 g) which was used without further purification. HPLC: $t_R$ 12.1 minutes.

B) $N^{15}$-tert-butyloxycarbonyl teicoplanin $A_2$ component 2 methyl ester [$N^{15}$-t-BOC CTA/2 methyl ester] (Formula I: X=COOMe, R=8-methylnonanoyl-β-D-glucosaminyl;

$R_1$=N-acetyl-β-D-glucosaminyl; $R_2$=α-D-Mannosyl).

To a stirred solution of 50 g of $N^{15}$-t-BOC CTA/2 (prepared in procedure A above) in 300 ml of dimethylformamide (DMF), $KHCO_3$ (6 g) and methyl iodide (3,5 ml) were added at room temperature. After 5 hours, the reaction mixture was poured into 2 l of $H_2O$. The resulting suspension was adjusted at pH 3.5 with 1N HCl and then extracted with 1 liter of BuOH. The organic layer was separated, washed with $H_2O$ (3×300 ml), and concentrated to a small volume (about 150 ml) at 40° C. under reduced pressure. On adding 350 ml of ethyl ether ($Et_2O$), the precipitated solid was collected, washed with $Et_2O$ (500 ml), and then dried in vacuo at room temperature overnight, to give 50 g of the title compound enough pure for the next step. HPLC: $t_R$ 15.0 minutes.

C) $N^{15}$-tert-butyloxycarbonyl deglucoteicoplanin [$N^{15}$-t-BOC-TD] (Formula I: X=COOH, R=$R_1$=$R_2$=H).

To a stirred solution of deglucoteicoplanin hydrochloride (1.25 g, 1 mmole) in DMF (20 ml) tert.-butyl 2,4,5-trichlorophenyl-carbonate (340 mg, 1.1 mmole, and triethylamine (0.7 ml) are added. The mixture is kept overnight at room temperature then water (200 ml) is added and the pH is adjusted to pH 2 by adding N HCl. The product is extracted with 150 ml of ethylacetate: BuOH 3:1 (v/v). The organic layers are collected and concentrated to about 40 ml; then ether (250 ml) is added. The suspension, after standing overnight at 0° C., is filtered, the recovered product is washed with ether and dried in vacuo at 50° C. Yield 1.1 g of the pure compound of the title.

D) $N^{15}$-tert-butyloxycarbonyl deglucoteicoplanin methyl ester [$N^{15}$-t-BOC-TD methyl ester] (Formula 1: X=COOMe, R=$R_1$=$R_2$=H).

To a stirred solution of $N^{15}$-t-BOC-TD deglucoteicoplanin (prepared according to the procedure C above) (500 mg, 0.385 mmole) in DMF (10 ml), finely ground $KHCO_3$ (40 mg) and methyl iodide (30 µl) are added. The mixture is stirred at room temperature until the reaction is completed (3 hours), then water (100 ml) is added and the mixture extracted three times with BuOH (100 ml). The organic extracts are washed with water and concentrated to 20 ml in vacuo at 50° C. The reaction product is precipitated by adding $Et_2O$ (200 ml). After standing overnight at 0° C., the product is collected by filtration, washed with $Et_2O$ and dried in vacuo at 50° C., yielding 320 mg of the compound of the title.

EXAMPLE 1

38-Decarboxy-38-hydroxymethyl teicoplanin $A_2$, component 2 [HM-CTA/2] (Formula I: X=$CH_2OH$; R=8-methyl-nonanoyl-β-D-glucosaminyl, $R_1$=N-Acetyl-β-D-glucosaminyl, $R_2$=α-D-Mannosyl; $R_3$= hydrogen).

To a stirred suspension of 18 g (about 9 mmol) of $N^{15}$-t-BOC-CTA/2 methyl ester (see procedure B above) in 1 liter of H$_2$O, 800 ml of a BuOH:Et$_2$O 1:1 (v/v) mixture was added to prevent foaming followed by 54 g (about 1.45 mol) of NaBH$_4$ pellets over a period of 60 minutes. Stirring was continued for 5 hours at room temperature, afterwards a solution of 100 ml of acetic acid (AcOH) in 100 ml of BuOH was slowly added while cooling at 20° C. Most Et$_2$O was evaporated and the resulting mixture was extracted with 1 liter of BuOH. The organic layer was washed with H$_2$O (2×500 ml), and then it was concentrated to a small volume (about 150 ml) at 50° C. under reduced pressure. On adding Et$_2$O (850 ml), the precipitated solid (about 15 g) was collected and re-dissolved in 100 ml of anhydrous trifluoroacetic acid (TFA). After 2 minutes, 100 ml of methanol (MeOH) was added followed by 800 ml of Et$_2$O. The precipitated solid was collected and quickly dissolved in 500 ml of a water: acetonitrile 9:1 (v/v) mixture. The resulting solution was adjusted at pH 7 with 1N NaOH and then loaded on a column of 750 g of silanized silica-gel in H$_2$O. The column was eluted with a linear gradient from 10% to 80% of acetonitrile in 0.1N AcOH in 18 hours at the flow rate of about 200 ml/h, while collecting 20 ml-fractions. Those fractions containing pure title compound were pooled and enough BuOH was added to obtain, after concentration of the resulting mixture at 40° C. under reduced pressure, a dry butanolic suspension of about 100 ml. On adding 400 ml of Et$_2$O, the precipitated solid was collected, washed with 500 ml of Et$_2$O, and then dried in vacuo at room temperature overnight, to yield 10.2 g of the product of the title as the free base.

EXAMPLE 2

38-Decarboxy-38-hydroxymethyl of teicoplanin pseudoaglycon 1 [HM-TB] (Formula I: X=CH$_2$OH, R=H, R$_1$=N-Acetyl-β-D-glucosaminyl, R$_2$=α-D-Mannosyl, R$_3$=hydrogen).

A solution of 500 mg (about 0.26 mmol) of HM-CTA/2 (as prepared in Example 1 above) in 5 ml of TFA was stirred at room temperature for 90 minutes, afterwards the solvent was evaporated at room temperature under reduced pressure. The oily residue was dissolved in 20 ml of H$_2$O. The resulting solution was adjusted at pH 8.0 with 1N NaOH and the precipitated solid was collected. After drying in vacuo at 35° C. overnight, 360 mg of the title compound was obtained, as the free base.

EXAMPLE 3

38-Decarboxy-38-hydroxymethyl of teicoplanin pseudoaglycon 2 [HM-TC] (Formula I: X=CH$_2$OH, R=R$_2$=H, R$_1$=N-Acetyl-β-D-glucosaminyl, R$_3$= hydrogen).

Dry HCl was bubbled at room temperature into a suspension of 1 g (about 0.52 mmol) of HM-CTA/2 (as prepared in Example 1 above) in 50 ml of 1,2-dimethoxyethane (DME) for 24 hours. The insoluble product was collected by filtration and purified by reverse-phase column chromatography as previously described for HM-CTA/2, yielding 180 mg of the title compound, as the free base.

EXAMPLE 4

38-Decarboxy-38-hydroxymethyl deglucoteicoplanin [HM-TD] (Formula I: X= CH$_2$OH, R=R$_1$=R$_2$=R$_3$ hydrogen).

To a stirred solution of 2 g (about 1.5 mmol) of N$^{15}$-t-BOC-TD methyl ester (see the procedure D above) in 100 ml of an ethanol: H$_2$O 1:1 (v/v) solution, 8 g (about 0.21 mol) of NaBH$_4$ pellets were added portionwise at room temperature over a period of 4 hours, afterwards 100 ml of MeOH was added. After stirring at room temperature for 1 hour, 25 ml of AcOH were added dropwise while cooling at 20° C. The resulting solution was diluted with 250 ml of H$_2$O and extracted with 30 ml of ethyl acetate. The organic layer was concentrated at 30° C. under reduced pressure to a small volume (about 50 ml). On adding 450 ml of Et$_2$O, the precipitated solid was collected and purified by reverse-phase column chromatography by eluting with a linear gradient from 10% to 50% of acetonitrile in 0.001N HCl. About 1.4 g of the title compound was obtained, as the hydrochloride, which was dissolved in 40 ml of H$_2$O. The resulting solution was adjusted at pH 8.5 with 1N NaOH and the precipitated solid was collected. After drying in vacuo at 40° C. overnight, 1.15 g of HM-TD was obtained, as the free base.

---

---

We claim:

1. A 38-decarboxy-38-hydroxymethyl teicoplanin derivative of formula I:

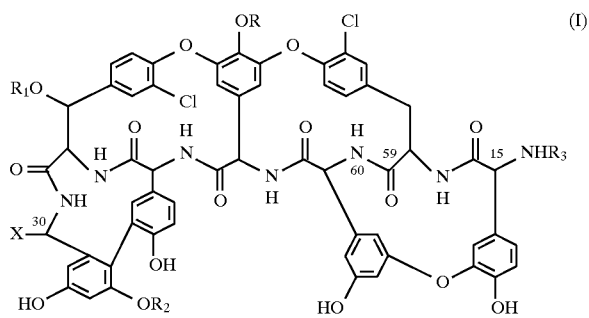

(I)

wherein:

X represents hydroxymethyl;

R represents hydrogen or —N[($C_9$–$C_{12}$)aliphatic acyl]-β-D-2-deoxy-2-aminoglucopyranosyl;

$R_1$ represents hydrogen or N-acetyl-β-D-2-deoxy-2-aminoglucopyranosyl;

$R_2$ represents hydrogen or α-D-mannopyranosyl, $R_3$ represents hydrogen or a protecting group of the amino function; or the acid addition salts thereof; with the proviso that $R_1$ represents hydrogen only when R and $R_2$ are simultaneously hydrogen.

2. A compound of claim 1 wherein X is hydroxy methyl, R is -8-methylnonanoyl-β-D-2-deoxy-2-2-aminoglucopyranosyl, $R_1$ is —N-Acetyl-β-D-2-deoxy-2-aminoglucopyranosyl, $R_2$ is α-D-mannopyranosyl and $R_3$ is hydrogen.

3. A compound of claim 1 wherein X is hydroxymethyl, R is hydrogen, $R_1$ is —N-Acetylβ-D-2-deoxy-2-aminoglucopyranosyl; $R_2$ is α-D-mannopyranosyl and $R_3$ is hydrogen.

4. A compound of claim 1 wherein X is hydroxymethyl R, $R_2$ and $R_3$ are hydrogen atoms and $R_1$ is —N-Acetyl-β-D-2-deoxy-2-aminoglucopyranosyl.

5. A compound of claim 1 wherein X is hydroxymethyl and R, $R_1$, $R_2$ and $R_3$ are hydrogen atoms.

6. A process for preparing a 38-decarboxy-38-hydroxymethyl derivative according to claim 1 which comprises:

a) submitting a teicoplanin lower alkyl ester derivative of formula II:

wherein:

$R_4$ represents ($C_1$–$C_4$)alkyl;

R represents hydrogen or —N[($C_9$–$C_{12}$)aliphatic acyl]-β-D-2-deoxy-2-aminoglucopyranosyl;

$R_1$ represents hydrogen or N-acetyl-β-D-2-deoxy-2-aminoglucopyranosyl;

$R_2$ represents hydrogen or α-D-mannopyranosyl;

$R_3$ represents a protecting group of the amino function; and the addition salts thereof; with the proviso that $R_1$ represents hydrogen only when R and $R_2$ are simultaneously hydrogen; to a reductive hydrolysis reaction with an alkali metal borohydride, at a temperature between 0° C. and 40° C., in the presence of water or a mixture of water and a water miscible organic co-solvent as solvent;

b) optionally transforming a 38-decarboxy-38-hydroxymethyl compound of formula I wherein R, $R_1$ and $R_2$ represent a sugar moiety as above defined into the corresponding compound wherein $R_1$ and $R_2$ are as above and R is hydrogen, by means of controlled acid hydrolysis in strong concentrated aqueous organic acid; or c) optionally transforming a 38-decarboxy-38-hydroxymethyl compound of formula I wherein R, $R_1$ and $R_2$ represent a sugar moiety as above defined or R represents hydrogen and $R_1$ and $R_2$ represent sugar moieties as above defined into the corresponding 38-decarboxy-38-hydroxymethyl compound of formula I wherein R and $R_2$ represent hydrogen and $R_1$ represents a sugar moiety as defined, by means of a selective hydrolysis with a strong acid in the presence of a polar aprotic solvent selected from ethers, ketones, and mixtures thereof which are liquid at room temperature; or d) optionally transforming a 38-decarboxy-38-hydroxymethyl compound of formula I wherein R, $R_1$, and $R_2$ represent sugar moieties as defined above, a 38-decarboxy-38-hydroxymethyl compound of formula I wherein R represents hydrogen and $R_1$ and $R_2$ represent the above defined sugar moieties, or a 38-hydroxymethyl compound of formula I wherein R and $R_2$ represent hydrogen, and $R_1$ represents a sugar moiety as above defined, into the corresponding compound of formula I wherein R, $R_1$ and $R_2$ represent

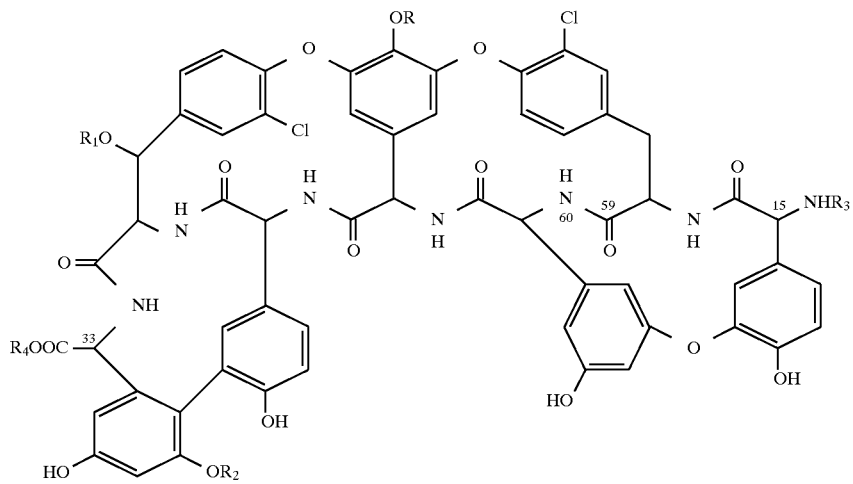

(II)

hydrogen atoms by means of a selective hydrolysis in an organic protic solvent selected from aliphatic acids and alpha-halogenated aliphatic acids which at the reaction temperature are liquids, aliphatic and cycloaliphatic alkanols which at the reaction temperature are liquids slightly mixable with water, phenyl-substituted lower alkanols wherein the phenyl moiety may optionally carry ($C_1$–$C_4$)alkyl, ($C_1$–$C_4$)alkoxy or halo moiety which at the reaction temperature are liquids slightly mixable with water, and β-polyhalogenated lower alkanols, which at the reaction temperature are liquids; in the presence of a strong acid, compatible with the solvent, selected from strong mineral acids, strong organic acids and strong acid cation exchange resins in the hydrogen form and at a temperature between 20° C. and 100° C.

7. A process as claimed in claim 6, optional step b), wherein the concentrated organic acid is 75 to 95% aqueous trifluoroacetic acid and the reaction temperature is between 10° and 50° C.

8. A process as claimed in claim 6, optional step c), wherein the strong acid is a concentrated mineral acid.

9. A process as claimed in claim 8 wherein the reaction solvent is dimethoxyethane and the reaction temperature is about room temperature.

10. A process as claimed in claim 6, optional step d), wherein the strong acid is a mineral acid, the solvent is a β-polyhalogenated lower alkanol and the hydrolysis is conducted at a temperature 65° C. and 85° C.

11. A pharmaceutical composition comprising a compound of claim 1 in admixture with a pharmaceutically acceptable carrier.

12. A method for the treatment of bacterial infections comprising administering a compound according to claim 1 to a patient in need thereof.

13. A compound of claim 1 wherein the —N[($C_9$–$C_{12}$) aliphatic acyl]-β-D-2-deoxy-2-aminoglucopyranosyl radicals of the symbol R is one of the following: (Z)-4-decenoyl, 8-methylnonanoyl, decanoyl, 8-methyldecanoyl, 9-methyldecanoyl, 6-methyloctanoyl, nonanoyl, 10-methylundecanoyl and dodecanoyl.

14. A process for preparing a compound as in claim 6 wherein the teicoplanin lower alkyl ester derivative of formula II wherein R, $R_1$ and $R_2$ are hydrogen atoms is submitted to a reductive alkylation in the presence of a mixture of water and water miscible organic co-solvent.

15. A process for preparing a compound as in claim 14 wherein the teicoplanin lower alkyl ester derivative of formula II wherein R, $R_1$ and $R_2$ are hydrogen atoms is submitted to a reductive alkylation in the presence of hydroalcoholic medium wherein the alcohol is a lower alkanol and the ratio of water to alkanol ranges between 90 to 10 and 40 to 60 volume to volume.

16. A process according to claim 15 wherein the ratio of water to alkanol ranges between 70 to 30 volume to volume and 50 to 50 volume to volume.

17. A process as claimed in claim 6 wherein the alkali metal borohydride is selected from the group consisting of sodium borohydride, potassium borohydride and sodium cyanoborohydride.

* * * * *